(12) United States Patent
Wu

(10) Patent No.: US 10,362,828 B2
(45) Date of Patent: Jul. 30, 2019

(54) HEADBAND ARRANGEMENT AND WELDING HELMET EQUIPPED WITH THE SAME

(71) Applicant: Tecmen Electronics Co., Ltd., Nanjing (CN)

(72) Inventor: Ziqian Wu, Nanjing (CN)

(73) Assignee: Tecmen Electronics Co., Ltd., Nanjing (CN)

( * ) Notice: Subject to any disclaimer, the term of this patent is extended or adjusted under 35 U.S.C. 154(b) by 128 days.

(21) Appl. No.: 15/409,025

(22) Filed: Jan. 18, 2017

(65) Prior Publication Data

US 2018/0042330 A1    Feb. 15, 2018

(30) Foreign Application Priority Data

Aug. 10, 2016 (CN) ............... 2016 2 0864542 U
Dec. 15, 2016 (CN) ............... 2016 2 1377700 U

(51) Int. Cl.
| | |
|---|---|
| *A42B 3/08* | (2006.01) |
| *A42B 3/32* | (2006.01) |
| *A61F 9/06* | (2006.01) |
| *A42B 3/14* | (2006.01) |
| *H01F 7/02* | (2006.01) |
| *F16P 1/04* | (2006.01) |

(Continued)

(52) U.S. Cl.
CPC ............... *A42B 3/085* (2013.01); *A42B 3/14* (2013.01); *A42B 3/324* (2013.01); *A61F 9/06* (2013.01); *H01F 7/0242* (2013.01); *A42B 3/225* (2013.01); *F16P 1/04* (2013.01); *F16P 1/06* (2013.01)

(58) Field of Classification Search
CPC ........... A42B 3/085; A42B 3/14; A42B 3/324; A42B 3/225; A61F 9/06; F16P 1/04; F16P 1/06
See application file for complete search history.

(56) References Cited

U.S. PATENT DOCUMENTS

| | | | |
|---|---|---|---|
| 2007/0245467 A1 | 10/2007 | Lilenthal et al. | |
| 2011/0023204 A1* | 2/2011 | Brace ............... | A42B 3/225 2/8.2 |
| 2012/0066872 A1 | 3/2012 | Eisenberger | |

(Continued)

OTHER PUBLICATIONS

European Patent Office, Partial European Search Report in European Patent Application No. 17151337 (dated Jul. 11, 2017).

(Continued)

*Primary Examiner* — Khaled Annis

(57) ABSTRACT

The present application provides a headband arrangement for a welding helmet, comprising: a fixed attachment structure; and a helmet mounting structure cooperating with the attachment structure, wherein at least two stopping positions are defined longitudinally between the attachment structure and the helmet mounting structure, the helmet mounting structure is selectively switchable between an unlocking state and a locking state, wherein in the unlocking state, the helmet mounting structure is slidable between the stopping positions relative to the attachment structure, and wherein in the locking state, the helmet mounting structure can be locked to one of the stopping positions relative to the attachment structure and can be kept there by a magnetic force generated between a pair of magnetic parts.

17 Claims, 9 Drawing Sheets

(51) Int. Cl.
F16P 1/06 (2006.01)
A42B 3/22 (2006.01)

(56) References Cited

U.S. PATENT DOCUMENTS

| | | |
|---|---|---|
| 2012/0144567 A1 | 6/2012 | Huh |
| 2014/0366253 A1 | 12/2014 | Gotti |
| 2015/0047154 A1 | 2/2015 | DeBien |
| 2015/0074877 A1* | 3/2015 | Huh .................. A42B 3/225 2/422 |
| 2016/0037854 A1 | 2/2016 | Durham et al. |

OTHER PUBLICATIONS

European Patent Office, Extended European Search Report in European Patent Application No. 17151337 (dated Oct. 16, 2017).

* cited by examiner

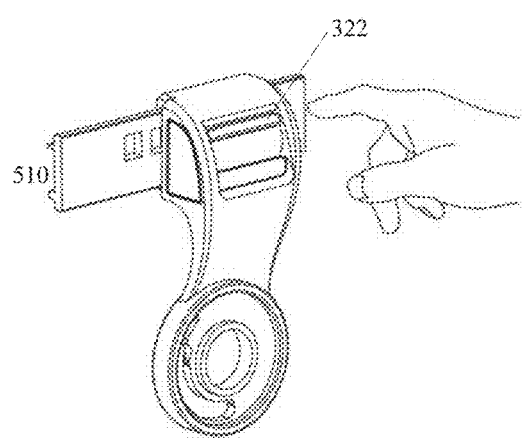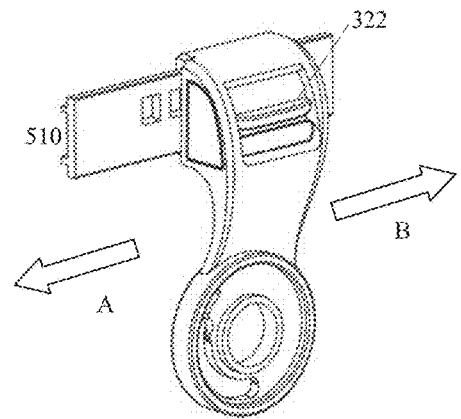
Fig. 4a   Fig. 4b
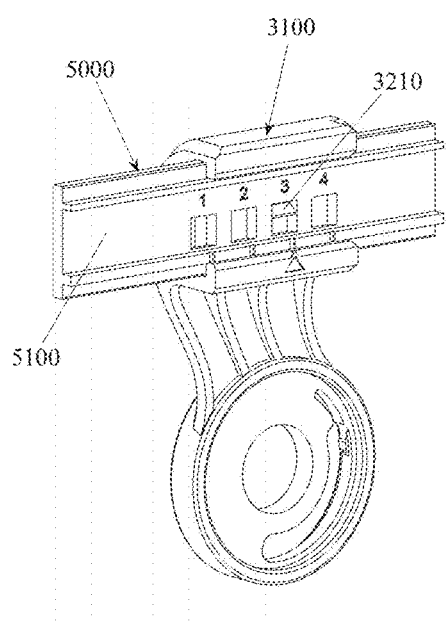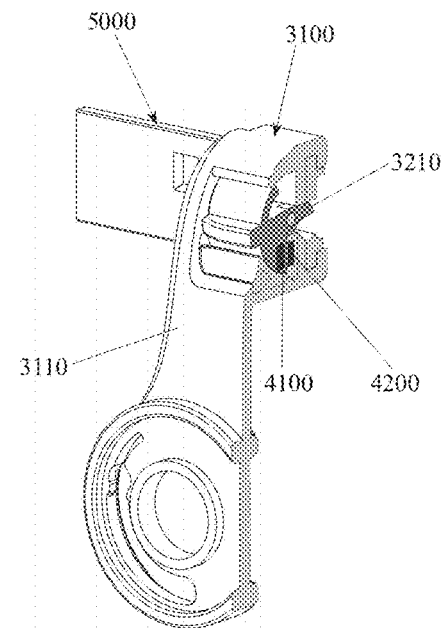
Fig. 5a

HEADBAND ARRANGEMENT AND WELDING HELMET EQUIPPED WITH THE SAME

CROSS-REFERENCE TO RELATED APPLICATIONS

This application claims the benefits of Chinese Patent Application No. 201620864542.8, filed on Aug. 10, 2016 and Chinese Patent Application No. 201621377700.3, filed on Dec. 15, 2016, the contents of which are incorporated herein by reference.

FIELD

The present application generally relates to a headband arrangement and a welding helmet, especially an auto-darkening welding helmet, equipped with the headband arrangement.

BACKGROUND

Welding helmets have become essential devices for protecting welders on welding sites. A welding helmet generally comprises a helmet shell and a headband arrangement disposed in the helmet shell. A protection sheet is mounted on the helmet shell to protect a welder's eyes. The headband arrangement is connected to the helmet shell and can be used to be directly worn on the welder's head.

A helmet mounting structure provided at a side of each ear of the welder is used to connect the headband arrangement to the helmet shell. If the welder can adjust the distance between his/her eyes and the protection sheet in case that the welding helmet is worn, it will be more helpful to protect the welder's eyes.

Further, in a conventional headband arrangement, no sufficient flexible cushion structure is provided at a location of protecting the back of the welder's head, such that the same headband arrangement cannot enable wearers whose heads have different shapes (especially the back of the head) to feel comfortable enough, which may indirectly impact the wearer's work efficiency.

SUMMARY

The present application is mainly aimed at providing an improved headband arrangement for the welding helmet, such that after the headband arrangement is worn on the wearer's head, it is easy for him/her to adjust the position of the headband arrangement relative to the welding helmet, and the worn headband arrangement can be more fitted for the shape of different wearers' heads and enable them to feel more comfortable.

In one aspect of the present application, a headband arrangement for a welding helmet is provided, the headband arrangement comprising: a fixed attachment structure; a helmet mounting structure cooperating with the attachment structure, wherein at least two stopping positions are defined longitudinally between the attachment structure and the helmet mounting structure, the helmet mounting structure is selectively switchable between an unlocking state and a locking state, wherein in the unlocking state, the helmet mounting structure is slidable between the stopping positions relative to the attachment structure, and wherein in the locking state, the helmet mounting structure can be locked to one of the stopping positions relative to the attachment structure and can be held there by a magnetic force generated between a pair of magnetic parts.

One key of the present application is to maintain the helmet mounting structure of the headband arrangement in its locking state by the magnetic force generated between the pair of magnetic parts.

Optionally, the helmet mounting structure comprises a lockable component which is mounted such that it is pivotable about a pivotal shaft in the helmet mounting structure, the pair of magnetic parts comprise a first magnetic part secured on the lockable component and a second magnetic part secured on the helmet mounting structure or the attachment structure; the helmet mounting structure can be switched between the unlocking state and the locking state by rotating the lockable component, and in the locking state, the helmet mounting structure is kept to be locked by a magnetic attractive or repulsive force generated between the first and second magnetic parts.

Optionally, the first magnetic part has a first magnetic side, and the second magnetic part has a second magnetic side; in case that the first magnetic side has the same magnetic polarity as the second magnetic side, the first and second magnetic parts are arranged such that as the lockable component is pivoted from the locking state to the unlocking state, the first magnetic side approaches the second magnetic side; or in case that the first magnetic side has a magnetic polarity different than the second magnetic side, the first and second magnetic parts are arranged such that as the lockable component is pivoted from the locking state to the unlocking state, the first magnetic side departs from the second magnetic side.

Optionally, the lockable component has a tongue, the stopping positions are defined by several location holes formed in the attachment structure, the tongue enters one of the location holes in the locking state, and the tongue leaves the location hole in the unlocking state to allow the helmet mounting structure to be longitudinally slidable.

Optionally, the helmet mounting structure has a bracket in which a socket is defined, and the pivotal shaft and the lockable component are disposed in the socket.

Optionally, the second magnetic part is disposed in the socket.

Optionally, the attachment structure has a location plate, the location holes are provided in the location plate, and a rail is provided in the location plate to guide the helmet mounting structure.

Optionally, the pivotal shaft is substantially parallel to the location plate.

Optionally, the second magnetic side of the second magnetic part is substantially parallel to the location plate.

Optionally, the lockable component has a handle which is exposed out of an opening of the socket to be accessible.

Optionally, an inserting component is received in the socket, the second magnetic part is securely provided in the inserting component, and the inserting component has an edge which defines a scope of moving of the handle in the opening of the socket.

In an alternative embodiment, the helmet mounting structure comprises a lockable component which is linearly movable in the helmet mounting structure, the pair of magnetic parts comprise a first magnetic part secured on the lockable component and a second magnetic part secured on the helmet mounting structure or the attachment structure; the helmet mounting structure can be switched between the unlocking state and the locking state by linearly moving the lockable component, and in the locking state, the helmet mounting structure is kept to be locked by a magnetic repulsive force generated between the first and second magnetic parts.

Optionally, the lockable component can be moved in a direction substantially perpendicular to a moving direction of the helmet mounting structure.

Optionally, the first and second magnetic parts are arranged such that they approach each other as the helmet mounting structure is being changed from the locking state to the unlocking state.

Optionally, the lockable component has a tongue, an elongated slot is formed in the attachment structure, the tongue protrudes into the slot, and the stopping positions are defined by several notches formed at a side of the slot and in communication with the slot, and wherein in the locking state, the tongue enters one of the notches, and in the unlocking state, the tongue leaves the notch to allow the helmet mounting structure to be longitudinally slidable.

Optionally, in the unlocking state, the tongue is longitudinally movable in the slot.

Optionally, the helmet mounting structure has a bracket in which a socket is defined, and the lockable component and the second magnetic part are disposed in the socket.

In an alternative embodiment the helmet mounting structure comprises a lockable component which is linearly movable in the helmet mounting structure, the pair of magnetic parts are disposed such that they are linearly movable in the helmet mounting structure, the pair of magnetic parts can be moved in a direction substantially perpendicular to a moving direction of the lockable component and parallel to a moving direction of the helmet mounting structure, the movement of the pair of magnetic parts is in association with the movement of the lockable component such that the helmet mounting structure can be switched between the unlocking state and the locking state, and in the locking state, the helmet mounting structure is kept to be locked by a magnetic repulsive force generated between the first and second magnetic parts.

Optionally, the lockable component has a tongue, the stopping positions are defined by several location holes formed in the attachment structure, the tongue enters one of the location holes in the locking state, and the tongue leaves the location hole in the unlocking state to allow the helmet mounting structure to be longitudinally slidable.

Optionally, the helmet mounting structure comprises a first key part and a second key part, the pair of magnetic parts comprise a first magnetic part embedded in the first key part and a second magnetic part embedded in the second key part, and the first and second magnetic parts approach each other as the helmet mounting structure is being changed from the locking state to the unlocking state.

Optionally, at least one of the first and second key parts is provided with a rod portion by which the lockable component can be driven to move.

Optionally, the rod portion has a linear section and an arc-shaped section, and the rod portion is inserted through a through-hole formed in the lockable component such that the rod portion can be moved substantially perpendicularly to the moving direction of the lockable component so as to pass through the through-hole.

Optionally, when the arc-shaped section of the rod portion passes through the through-hole, the lockable component is driven to move.

Optionally, when the crest of the arc-shaped section is located in the through-hole, the helmet mounting structure is in the unlocking state.

Optionally, the first and/or second magnetic part is a permanent magnet.

In another aspect of the present application, a headband arrangement for a welding helmet is provided, the headband arrangement comprising a band part for attaching at or adjacent to the back of a user's head, wherein the band part is provided with a sheath for adjusting the band part's length, a cushion structure is installed at a side of the sheath facing the back of the user's head, and wherein between the side of the sheath facing the back of the user's head and the cushion structure, two pivotal pins are provided adjacent to two lateral edges of the sheath such that the cushion structure can be pivoted about the two pivotal pins relative to the sheath.

Optionally, the cushion structure comprises two loop sections which are connected by a connection section, and each loop section has a support rib on which the pivotal pin is formed.

Optionally, two lugs are provided on the side of the sheath facing the back of the user's head, each lug is formed with a hole, the holes of the lugs are substantially coaxial with each other or their central axes include a small angle, and a respective pivotal pin can be inserted in a respective hole such that the cushion structure can be pivoted relative to the sheath.

Optionally, the cushion structure comprises two loop sections which are connected by a connection section, each loop section has a support rib for the pivotal pin, a hole is formed in each support rib, the holes of the support ribs are substantially coaxial with each other or their central axes include a small angle, two lugs are provided on the side of the sheath facing the back of the user's head, the pivotal pines are formed on the lugs respectively, and a respective pivotal pin can be inserted in a respective hole such that the cushion structure can be pivoted relative to the sheath.

Optionally, the pivotal pins are inserted into the holes by bending the cushion structure from its lateral edges towards its center.

Optionally, a sweat-absorbing pad is provided on a side of the cushion structure facing the back of the user's head.

In another aspect of the present application, a welding helmet equipped with said headband arrangement is provided.

Optionally, said welding helmet is an auto-darkness welding helmet.

BRIEF DESCRIPTION OF THE DRAWINGS

As a part of the description and in order to provide further explanation of the present invent, the drawings illustrate preferred embodiments of the present invention, and together with the description are used to explain the principle of the present invention. In the drawings:

FIGS. 4a and 4b schematically illustrate how to adjust the helmet mounting structure relative to the headband arrangement;

FIGS. 5a and 5b schematically illustrate that a helmet mounting structure according to another embodiment of the present application is in the locking state and the unlocking state respectively;

DETAILED DESCRIPTION OF EMBODIMENTS

Figure 1:
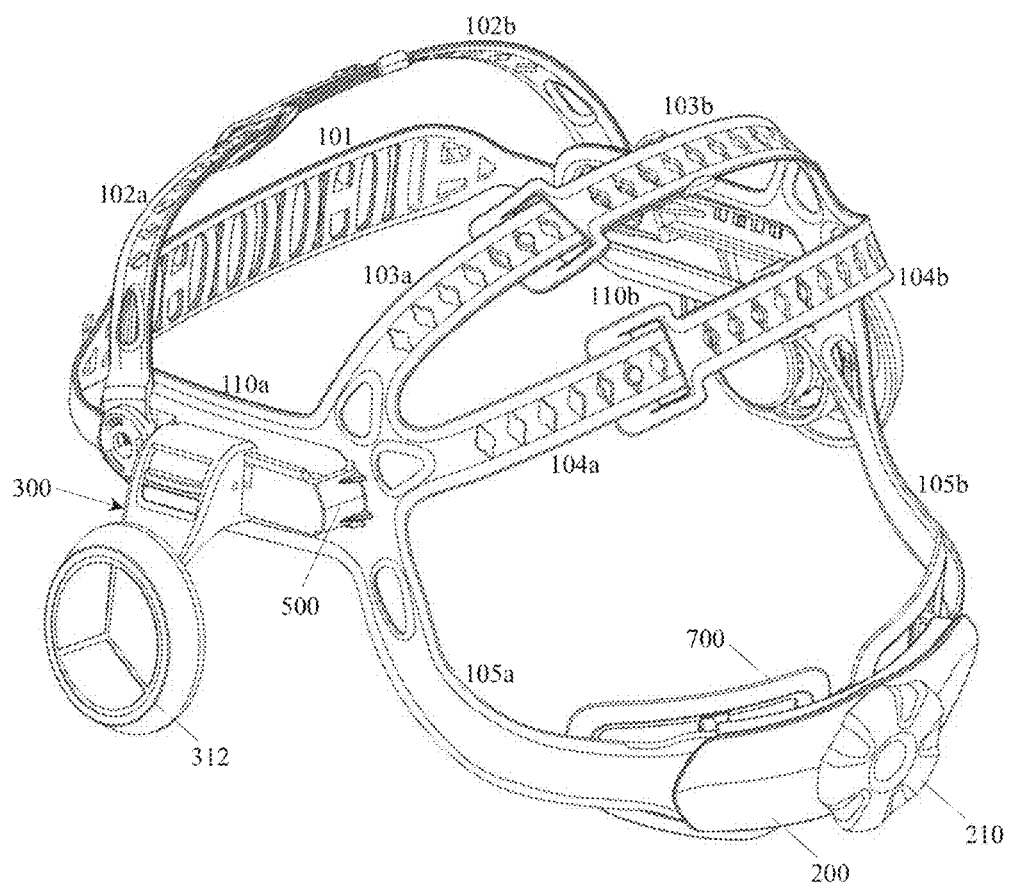
FIG. 1 is a perspective view schematically illustrating a headband arrangement for a welding helmet according to an embodiment of the present application.

In the drawings of the present application, the same or similar features are represented by the same reference numerals.

FIG. 1 is a perspective view schematically illustrating a headband arrangement 10 for a welding helmet (not shown) according to an embodiment of the present application. It is noted that in the context of the present application, the cited welding helmet can be also used to refer to an auto-darkening welding helmet. Generally, the welding helmet comprises a helmet shell and the headband arrangement 10 disposed within the helmet shell. In order to protect eyes of a wearer who will do welding work, a protection sheet is mounted on the helmet shell.

The headband arrangement 10 can be made of a plastic material. As shown in FIG. 1, the headband arrangement comprises several band parts 101, 102a, 102b, 103a, 103b, 104a, 104b, 105a, and 105b. The band part 101 is used to bear against the wearer's forehead. The band parts 102a, 102b, 103a, 103b, 104a, and 104b are used to bear against the top of the wearer's head. The band parts 105a and 105b are used to attach at or around the back of the wearer's head.

The headband arrangement 10 also comprises two lateral band parts 110a and 110b. The band parts 103a, 104a, and 105a are provided to extend integrally from the lateral band part 110a. The band parts 103b, 104b, and 105b are provided to extend integrally from the lateral band part 110b. For instance, each of pairs of the band parts 102a and 102b, 103a and 103b, and 104a and 104b are provided with an engaging structure therebetween by which the tightness of the headband arrangement 10 to be worn can be adjusted.

Further, each of the band parts 105a and 105b is provided with a toothed slot at one end. The ends of the two band parts can be inserted into a rear sheath 200 (FIG. 9) made of a plastic material in such a way that the ends are partly overlapped. A rotary knob 210 is rotatably installed on the rear sheath 200. A gear cooperating with the rotary knob 210 is provided in the rear sheath 200. The gear also engages with the toothed slots of the band parts 105a and 105b such that by positively or negatively rotating the knob 210, the two band parts 105a and 105b can be displaced with respect to each other to adjust the tightness of the headband arrangement 10.

The band parts 101, 102a, and 102b are pivotably connected to the lateral band parts 110a and 110b respectively such that when the headband arrangement 10 is worn by the wearer, the band parts 101, 102a, and 102b are more fitted for the forehead of wearers whose heads have different shapes.

An attachment structure 500 is provided on each of the lateral band parts 110a and 110b of the headband arrangement 10, and is used to cooperate with a respective helmet mounting structure 300. For instance, the lateral band part can be integrally formed with the attachment structure. The helmet mounting structure 300 is used to be secured in a corresponding fixation hole of the welding helmet so as to secure the headband arrangement 10 to the welding helmet.

Using the helmet mounting structure 300 according to the embodiment, the wearer can readily adjust the position of the welding helmet relative to the headband arrangement 10 forwards or backwards after the welding helmet is worn by him/her. Because the helmet mounting structures 300 at both lateral sides of the headband arrangement 10 are symmetrically provided, only the helmet mounding structure 300 cooperating with the attachment structure 500 on the lateral band part 110a now will be explained with respect to FIGS. 2 to 4b. A skilled person in the art should understand that contents of the explained helmet mounting structure can be applied for the attachment structure 500 on the other lateral band part 110b.

Figure 2:
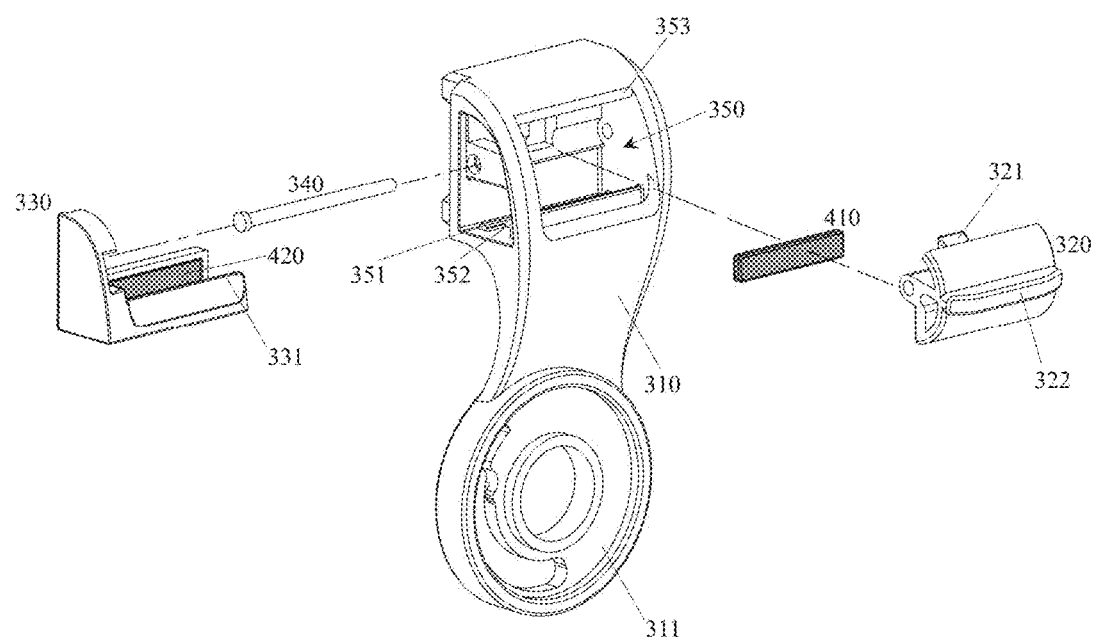
FIG. 2 is an exploded and perspective view schematically illustrating a bracket of a helmet mounting structure of the headband arrangement of FIG. 1.

As shown in FIG. 2, the helmet mounting structure 300 comprises a bracket 310. A knob mating part 311 is provided at one end of the bracket 310 to mate with a knob 312 (see FIG. 1) such that it can be secured in a mounting hole of the welding helmet. The bracket 310 is formed with a socket 350 at an end opposing the knob mating part 311. Housed in the socket 350 are a pivotal shaft 340 and a lockable component 320 which is pivotable about the pivotal shaft 340. For example, an inserting component 330 can be inserted in the socket 350 of the bracket 310.

In the embodiment shown by FIG. 2, the pivotal shaft 340 and the inserting component 330 can be installed into the socket 350 through a lateral opening of the bracket 310 and the lockable component 320 can be installed into the socket 350 through another lateral opening of the bracket 310, such that the pivotal shaft 340 can pass through both a hole of the bracket 310 in the socket 350 and a hole of the lockable component 320 to enable the lockable component 320 to be pivotable about the pivotal shaft 340. A handle 322 is integrally formed in an outer surface of the lockable component 320. When the lockable component 320 is assembled in place, the inserting component 330 causes the area of the opening, through which the lockable component 320 is installed, of the bracket 310 to be narrowed and the handle 322 can be exposed out of the opening of the bracket 310 such that the handle is accessible by one's finger. An edge 331 of the inserting component 330 and an edge 353 of the opening of the bracket 310 limit a range in which the handle 322 is movable. That is to say, the lockable component 320 can be pivoted in the socket 350 about the pivotal shaft 340 only in an angular range prescribed by the edges 331 and 353.

Figure 3A:
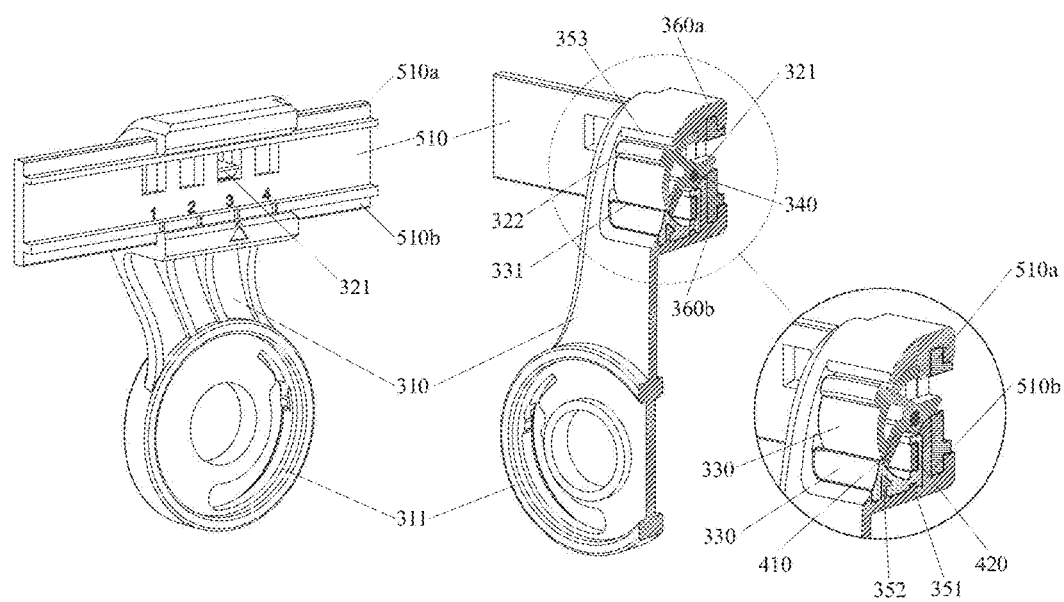
FIGS. 3a and 3b schematically illustrate that the helmet mounting structure is in a locking state and an unlocking states respectively.
Figure 3B:
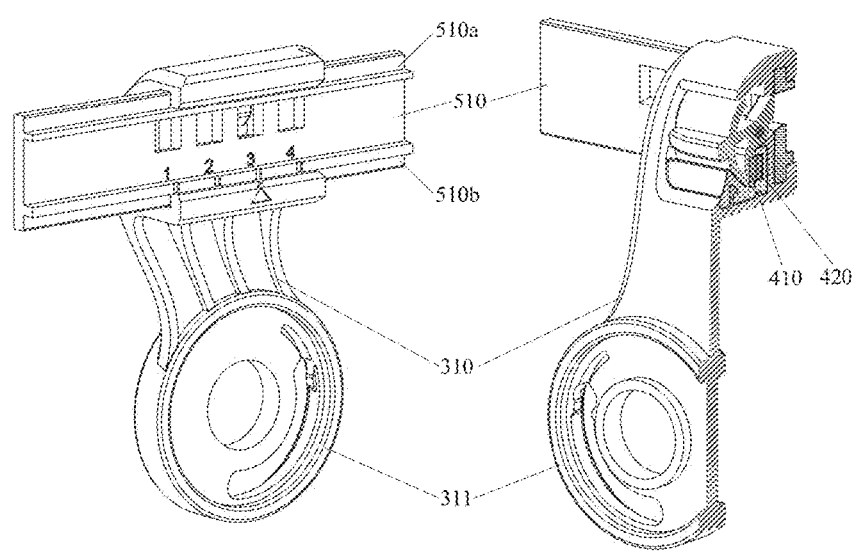

Further as shown in FIGS. 3a and 3b, a guiding rib 351 and a snapping rib 352 are formed in the socket 350. These ribs are used to engage corresponding grooves of the inserting component 330 so as to secure the inserting component 330 in the socket 350. A groove is formed in the inserting component 330 to receive a magnetic part 420, and a groove is formed in the lockable component 320 to receive a magnetic part 410. In the illustrated embodiment, the magnetic part 410, 420 is a flat and cubical body. In an alternative embodiment, the magnetic part can be shaped as a plate. In another alternative embodiment, the magnetic parts 420 and 410 can be adhered to the inserting component 330 and the lockable component 320 by an adhesive respectively. Each magnetic part has N and S magnetic polarities in its opposite surfaces respectively.

Each attachment structure 500 has a location plate 510. At least two location holes are longitudinally formed in the location plate 510 longitudinally. For instance, in FIGS. 3a and 3b, four location holes are formed. A pair of rails 510a and 510b are formed in two opposite longitudinal edges of the location plate 510 respectively. As shown in FIGS. 3a and 3b, a pair of grooves 360a and 360b is formed at a side of the bracket 310 opposite to the socket 350. The grooves 360a and 360b can engage the rails 510a and 510b respectively such that the bracket 310 can be longitudinally guided and moved along the location plate 510. The pivotal shaft 340 can be substantially parallel to the location plate 510. The magnetic part 420 can also be substantially parallel to the location plate 510.

A (lock) tongue 321 is integrally formed in the lockable component 320 at a location substantially opposing the handle 322. An opening is formed in a wall of the bracket 310, which wall forms part of the socket 350 and faces the location plate 510. For instance, when the lockable component 320 is pivoted about the pivotal shaft 340 into a locking state where the component contacts the edge 353, the tongue 321 of the lockable component 320 can pass through the opening of the wall of the bracket 310 and one location hole of the location plate 510 such that the bracket 310 is longitudinally locked with respect to the location plate 510. The magnetic parts 410 and 420 are arranged in the lockable and inserting components 320 and 330 respectively in such a way that circumferentially opposing surfaces or substantially opposing surfaces of the two magnetic parts have the same magnetic polarity. In case that the magnetic part 420 is omitted, the lockable component 320 in the locking state shown in FIG. 3a will pivot downwards about the pivotal shaft 340 due to the component's gravity. However, due to the existence of the magnetic part 420, a repulsive force generated between the magnetic parts 410 and 420 due to the same magnetic polarity repels the gravity to enable the lockable component 320 to be held in the locking state.

In a preferred embodiment, the magnetic part can be a permanent magnet, for example a NdFeB magnet, an AlNiCo magnet, an ferrite magnet or any other suitable magnet. The magnetism of the magnetic parts 410 and 420 should be designed such that the repulsive force generated between them is sufficient to drive the lockable component 320 to pivot about the pivotal shaft 340 into the locking state and to be kept there immovable. Further, the repulsive force should be not so great that it is hard to move the magnetic parts 410 and 420 close to each other.

When the lockable component 320 is pivoted about the pivotal shaft 340 into an unlocking state where the magnetic parts 410 and 420 bear against each other, the tongue 321 can leave the location hole of the location plate 510 and retract into the opening of the wall of the bracket 310 such that the tongue 321 will not hamper longitudinal sliding of the wall of the bracket 310 over the plate 510 under guidance of the rails 510a and 510b. When the lockable component 320 is in the unlocking state, the repulsive force between the magnetic parts 410 and 420 reaches its maximum. Therefore, after the bracket 310 is moved along the location plate 510 to a position relating to another location hole, the lockable component 320 can be pivoted into the locking state by the repulsive force such that the tongue 321 enters said another location hole to lock the bracket 310 to the location plate 510.

FIGS. 4a and 4b schematically illustrate how the helmet mounting structure according the embodiment is adjusted with respect to the headband arrangement. FIG. 4a illustrates that the helmet mounting structure 300 is normally in the locking state. It can be thought that the welding helmet (not shown) has been secured to the helmet mounting structure 300 in place. A space/gap is left between the welding helmet and the headband arrangement 10, which space/gap is large enough so as to allow a finger of the wearer to enter. When it is desirable to move the welding helmet relative to the headband arrangement 10, the finger of the wearer first presses the handle 322 to enable the tongue 321 of the helmet mounting structure 300 to leave the location hole where the tongue is located, such that the helmet mounting structure 300 can be in the unlocking state. Then, as shown in FIG. 4b, after the helmet mounting structure 300 is moved along an arrow A or B to a stopping position relating to another location hole with the helmet mounting structure 300 being held in the unlocking state, the handler 322 is released such that the tongue 321 enters said another location hole and thus the helmet mounting structure 300 is locked to the location plate 510 again.

As shown in FIGS. 3a and 3b, four location holes in the location plate 510 define four stopping positions 1, 2, 3, 4 to which the welding helmet can be moved forwards or backwards, such that the wearer can readily adjust the distance between the protection sheet and his/her eyes without taking off the welding helmet.

In the already mentioned embodiments, the helmet mounting structure 300 or the welding helmet is locked by the repulsive force between the two magnetic parts. Such contactless locking can be carried out conveniently. No spring element is needed in the helmet mounting structure 300, and thus its configuration is simplified and its lifetime is prolonged.

The helmet mounting structure is not limited to those embodiments explained previously. For instance, in an alternative embodiment, the inserting component 330 can be omitted, and the magnetic part 420 can be directly provided in the wall of the bracket 310 facing the location plate 510. In another alternative embodiment, the magnetic part 420 even can be directly provided in the location plate 510 as long as the repulsive force between the two magnetic parts 410 and 420 is great enough to drive the lockable component 320 to pivot about the pivotal shaft 340 into the locking state and thus to be kept immovable there. In this embodiment, even the wall of the bracket 310 facing the location plate 510 can be omitted. In another alternative embodiment, the magnetic parts 410 and 420 can be arranged such that they do not contact each other in the unlocking state; however, the repulsive force generated between the magnetic parts in the unlocking state should be greater than that generated in the locking state.

In an alternative embodiment, the location hole and the tongue can be interchanged with each other. For example, one location hole can be provided in part of the lockable component 320, and several tongues can be provided in the location plate 510. In this case, the stopping positions of the location plate 510 will be defined by the tongues. The bracket 310 will be redesigned such that when the lockable component 320 is in the unlocking state, no tongue enters the location hole and the bracket 310 can be slid along the location plate 510; and when the lockable component 320 is in the locking state, one tongue enters the location hole to prevent the bracket 310 from sliding along the location plate 510.

Figure 5B:
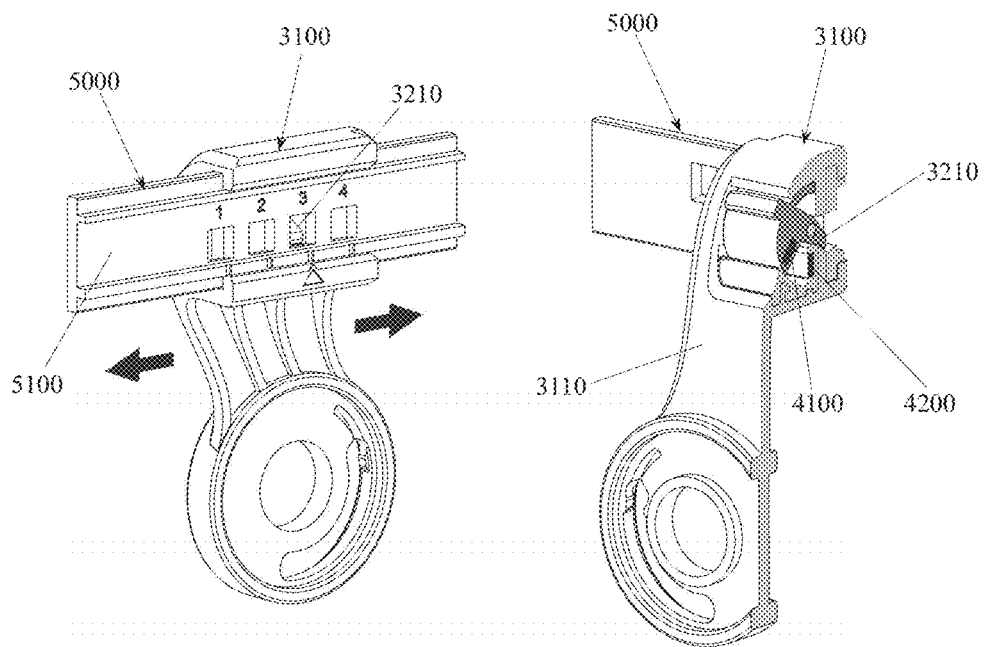

FIGS. 5a and 5b schematically illustrate that a helmet mounting structure 3100 according to another embodiment of the present application is in the locking state and the unlocking state respectively. The helmet mounting structure 3100 is able to cooperate with an attachment structure 5000 of the headband arrangement 10. The attachment structure 5000 can be configured similarly to the attachment structure 500. However, the location holes of the attachment structure 5000 are at a level slightly lower than the location holes of the attachment structure 500. The helmet mounting structure 3100 has a bracket 3110. A socket is formed in the bracket. A pivotal shaft is received in the socket and a lockable component, which can be pivoted about the pivotal shaft, is also received in the socket. An inserting component can be also received in the socket of the bracket. The bracket 3110, and the socket, the pivotal shaft, the lockable component and the inserting component thereof can be configured and arranged in a way similar to the bracket 310, the socket 350, the pivotal shaft 340, the lockable component 320 and the inserting component 330 illustrated by FIGS. 1 to 4b. Therefore, only the difference between the helmet mounting structure 3100 and the helmet mounting structure 300 will be explained below. A magnetic part 4100 and a magnetic part 4200 are arranged in the lockable component and the inserting component of the bracket 3110 respectively such that circumferentially opposing surfaces or substantially opposing surfaces of the two magnetic parts have different magnetic polarities. In this way, in a locking state illustrated by FIG. 5a, since a magnetic attractive force is generated between the two magnetic parts 4100 and 4200, the lockable component will be naturally pivotable about the pivotal shaft such that a tongue 3210 of the lockable component can enter one location hole of a location plate 5100 of the attachment structure 5000. Therefore, the bracket 3110 can be longitudinally locked relative to the location plate 5100. In an unlocking state illustrated by FIG. 5b, with the action of an external force (for example, by toggling the handle of the lockable component with one's finger), the lockable component can overcome the magnetic attractive force generated between the magnetic parts 4100 and 4200 so as to pivot about the pivotal shaft. Therefore, the tongue 3210 of the lockable component can leave the location hole of the location plate 5100 such that the bracket 3110 is enabled to be longitudinally slidable along the location plate 5100. In the embodiment, the magnetic intensity of the magnetic parts 4100 and 4200 should be designed such that the magnetic attractive force between them can ensure that the tongue 3210 of the lockable component can be reliably kept in the location hole of the location plate 5100 and the magnetic attractive force will be not so strong that a user cannot toggle the lockable component.

Figure 6A:
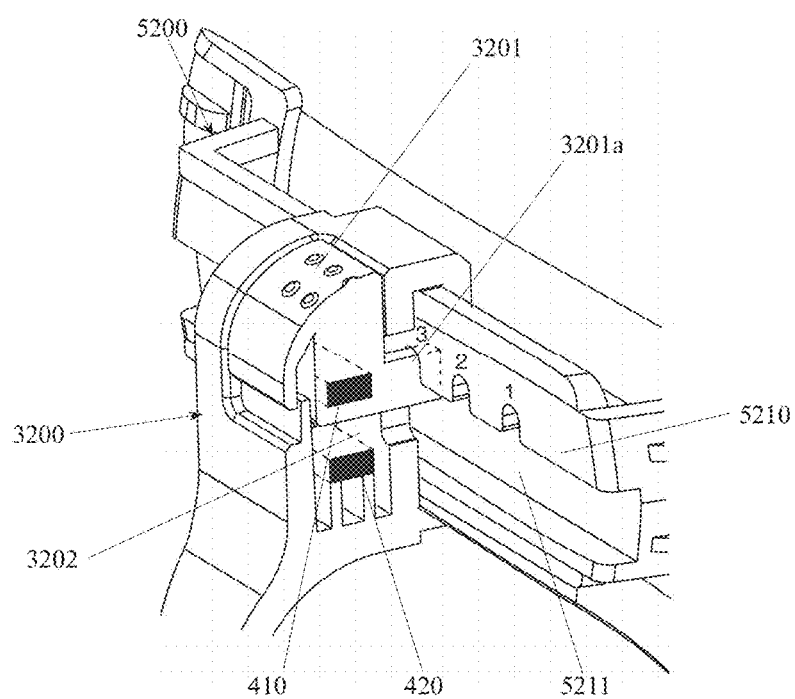
FIG. 6a schematically illustrates a partial and perspective view of a headband arrangement according to another embodiment of the present application, wherein the headband arrangement's helmet mounting structure is in the locking state.
Figure 6B:
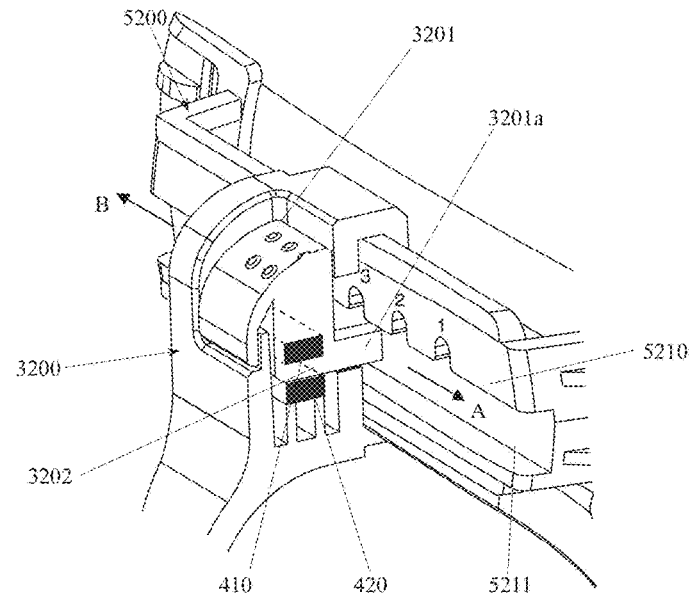
FIG. 6b schematically illustrates that the helmet mounting structure of FIG. 6a is in the unlocking state.

FIGS. 6a and 6b schematically illustrate a headband arrangement according to another embodiment of the present application for a welding helmet (not shown) in a partial and perspective view. This headband arrangement is distinguished from the headband arrangement 10 mainly by an attachment structure 5200 and a helmet mounting structure 3200. The headband arrangement illustrated by FIGS. 6a and 6b is provided with the attachment structure 5200. It is appreciated that both the attachment structure 5200 and the helmet mounting structure 3200 are provided at either lateral side of the headband arrangement.

Each attachment structure 5200 comprises a location plate 5210. This location plate 5210 can be used, in a way similar to the location 510, to guide the helmet mounting structure 3200 to slide along it. A longitudinal slot is formed in the location plate 5210. Several notches are also formed in the location plate 5210 so that they are in communication with the slot. For example, in FIGS. 6a and 6b, the notches open downwards.

Each helmet mounting structure 3200 comprises a button 3201 and a socket 3202 in which the button is slidably received. When the helmet mounting structure 3200 has been fitted onto the attachment structure 5200, a sliding direction of the button 3201 is substantially perpendicular to a sliding direction of the helmet mounting structure 3200. The button 3201 is formed with a tongue 3201a. The tongue 3201a extends perpendicularly to the sliding direction of the button 3201. Furthermore, after the helmet mounting structure 3200 is fitted onto the attachment structure 5200, the tongue 3201a can protrude into the slot of the location plate 5210.

The magnetic parts 410 and 420 are secured in the button 3201 and the socket 3202 respectively, such that the circumferentially opposing surfaces or substantially opposing surfaces of the two magnetic parts have the same magnetic polarity. For instance, the magnetic part 410 is adhered to a downwards opening recess of the button 3201, and the magnetic part 420 is adhered to a bottom side of the socket 3202. In case that the magnetic part 420 is omitted, the button 3201 will slide downwards in the socket 3202 by gravity. However, due to the existence of the magnetic part 420, a magnetic repulsive force generated between the magnetic parts 410 and 420 will bias the button 3201 upwards against gravity.

FIG. 6a shows that the helmet mounting structure 3200 is in the locking state. In this locking state, due to the magnetic repulsive force between the magnetic parts 410 and 420, the button 3201 is biased upwards so that the tongue 3201a can engage into one notch of the location plate 5210. Therefore, the helmet mounting structure 3200 can be longitudinally locked relative to the attachment structure 5200.

FIG. 6b shows that the helmet mounting structure 3200 is in the unlocking state. In this unlocking state, the user presses the button 3201 by his/her finger such that the button 3201 can be slid downwards in the socket 3202 and the tongue 3201a disengages from the notch of the location plate 5210. In the meanwhile, the tongue 3201a enters the slot of the location plate 5210 and the helmet mounting structure 3200 is allowed to be longitudinally slidable along the attachment structure 5200 (for example, as shown by arrows A and B of FIG. 6b). After the button 3201 arrives at a stopping position corresponding to another notch of the location plate 5210, the button is released such that the tongue 3201a can engage into said another notch and the helmet mounting structure 3200 is longitudinally locked relative to the attachment structure 5200 again.

In an alternative embodiment, the magnetic part 410 is disposed on the button 3201 and the magnetic part 420 is disposed on the attachment structure 5200 such that the two magnetic parts 410 and 420 approach each other as the helmet mounting structure is being changed from the locking state to the unlocking state.

Figure 7:
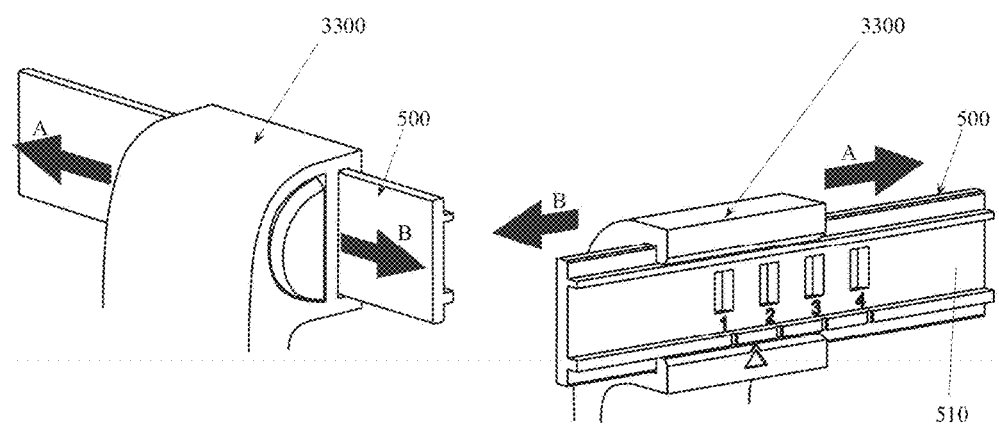
FIG. 7 schematically illustrates a partial and perspective view of a headband arrangement according to another embodiment of the present application.

FIG. 7 is a partial and perspective view schematically showing a headband arrangement for a welding helmet (not shown) according to another embodiment of the present application. This headband arrangement is distinguished from the headband arrangement 10 mainly by a helmet mounting structure 3300. The headband arrangement of FIG. 7 can be equipped with the attachment structure of FIGS. 1 to 6b. The helmet mounting structure 3300 can cooperation with the attachment structure.

Figure 8A:
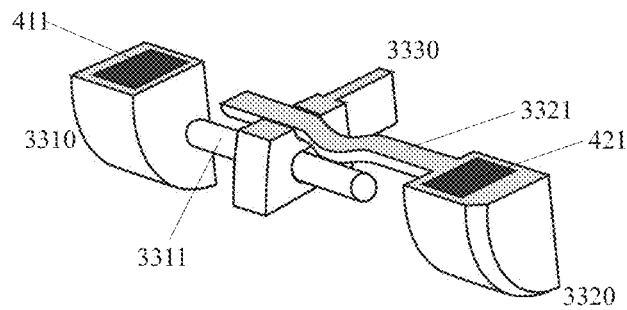
FIG. 8a is a partially cross-sectional and perspective view schematically showing a helmet mounting structure for the headband arrangement of FIG. 7.

Now, the configuration of the helmet mounting structure 3300 will be explained with regard to FIG. 8a. The helmet mounting structure 3300 comprises a bracket. A key part 3310 and a key part 3320 are installed in the bracket. The two key parts 3310 and 3320 are at least partially exposed at both sides of the bracket such that they can be pressed by the user. The key parts 3310 and 3320 are provided in the bracket such that they can be guided to slide towards or far away from each other. The key parts 3310 and 3320 can be slid in a direction substantially perpendicular to a sliding direction of the helmet mounting structure 3300 over the attachment structure 500. Either of the key parts is provided with a rod portion at a side facing the other key part. For instance, the key part 3310 is provided with a rod portion 3311, and the key part 3320 is provided with a rod portion 3321. The length of the two rod portions is sized such that the sliding of the key parts is not negatively affected. The two rod portions 3311 and 3321 are arranged in the bracket such that they are parallel to each other. In the interior of the bracket, a tongue 3330 is also provided between the two key parts 3310 and 3320. The tongue 3330 is arranged in the bracket such that it can be guided to be freely slidable in a direction substantially perpendicular to both the sliding direction of the key parts 3310 and 3320 and the sliding direction of the helmet mounting structure 3300. Like the tongue 321, the tongue 3330 can partly protrude out of the bracket such that it can enter one location hole of the location plate 510

One of the two rod portions (for example, the rod portion 3321) is substantially in the form of a linear rod but having an arc-shaped section. The other of the two rod portions (for example, the rod portion 3311) is substantially in the form of a linear rod. Each rod has a substantially constant cross-section. The tongue 3330 is formed with a through-hole and an elongated slot. The cross-section of the through-hole is complementary to the cross-section of the rod portion 3321 such that the rod portion 3321 is allowed to pass and slide through the through-hole without clearance. The length of the elongated slot is not less than the arc-height of the rod portion 3321. In other words, the cross-section of the elongated slot is greater than that of the rod portion 3321. After the key parts 3310 and 3320 and the tongue 3330 are assembled in place in the bracket of the helmet mounting structure 3300, the rod portion 3321 passes through the through-hole of the tongue 3330 and the rod portion 3311 passes through the elongated slot of the tongue 3330. In this way, when the key parts 3310 and 3320 are moved towards each other, the arc-shaped section of the rod portion 3321 can be moved through the through-hole of the tongue 3330. In the meanwhile, driven by the arc-shaped section of the rod portion 3321, the tongue 3330 is movable in a direction perpendicular to a moving direction of the key parts 3310 and 3320.

The key parts 3310 and 3320 are embedded with a magnetic part 411 and a magnetic part 412 respectively. Like the magnetic parts 410 and 420, the magnetic parts 411 and 412 are arranged such that the opposing surfaces or substantially opposing surfaces of the two magnetic parts have the same magnetic polarity. When being free from an external force, the key parts 3310 and 3320 will be moved apart from each other under the action of a magnetic repulsive force generated between the magnetic parts 411 and 421. It is conceivable that a stopper can be provided between the key part and the bracket such that the key part can only partly protrude out of the bracket.

Figure 8B:
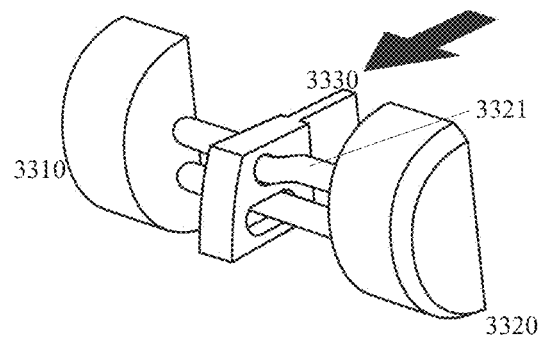
FIGS. 8b and 8c schematically illustrate that the helmet mounting structure of FIG. 7 is in the locking state and the unlocking state respectively.

FIG. 8b shows that the helmet mounting structure 3300 is in the unlocking state. The user can press the key parts 3310 and 3320 to enable them to overcome the magnetic repulsive force between the magnetic parts 411 and 421 in the helmet mounting structure 3300 and thus to be slidable towards each other. As the arc-shaped section of the rod portion 3221 is slid through the through-hole of the tongue 3330, the tongue 3330 is driven to move along a direction towards the crest of the arc-shaped section. With the tongue 3330 being driven, the rod portion 3310 is longitudinally slid in the elongated slot of the tongue 3330 in such a way that the movement of the tongue 3330 is not affected. When the crest of the arc-shaped section is in the through-hole of the tongue 3330, the tongue 3330 is moved to its extreme extent. Now, the tongue 3330 retracts into the bracket and does not enter any location hole of the location plate 510. Therefore, the helmet mounting structure 3300 is allowed to be longitudinally slidable relative to the attachment structure 500, especially the location plate 510.

Figure 8C:
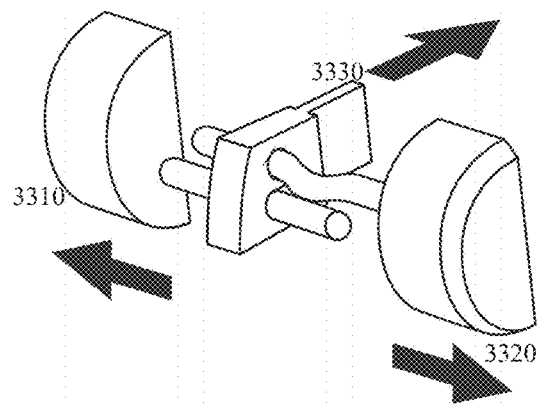

FIG. 8c illustrates that the helmet mounting structure 3300 is in the unlocking state. The key parts 3310 and 3320 are released such that with the action of the magnetic repulsive force between the magnetic parts 411 and 421, the key parts 3310 and 3320 are moved away from each other. In this process of moving, the crest of the arc-shaped section leaves the through-hole of the tongue 3330 and, finally, a linear section of the rod portion 3321 passes through the through-hole of the tongue 3330 such that the tongue 3330 protrudes out of the bracket again. Therefore, the tongue 3330 can enter one location hole of the location plate 510 by its free end such that the helmet mounting structure 3300 can be longitudinally locked to the attachment structure 500, especially the location plate 510.

In an alternative embodiment, even the rod portion 3311 can be omitted from the key part 3310. That is to say, only the rod portion 3321 of the key part 3320 can be used to move the tongue 3330 as mentioned above.

Figure 9:
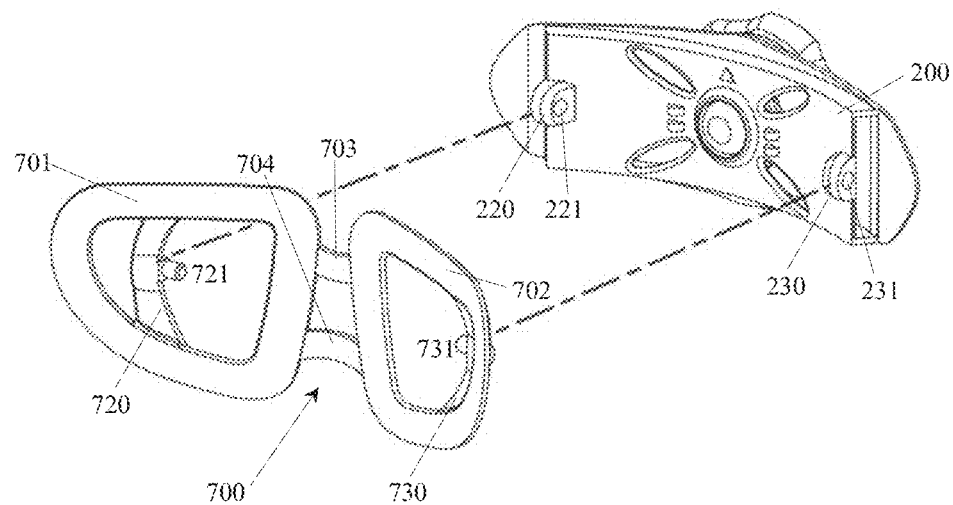
FIG. 9 schematically illustrates a cushion structure according to one embodiment of the present application, which is located on a rear sheath of the headband arrangement.

Turning to FIG. 9, a cushion structure 700 according to an embodiment of the present application is illustrated. The cushion structure 700 is installed on the rear sheath 200 such that the cushion structure can be pivoted to a certain extent to contact the back of the wearer's head. Two lugs 220 and 230 are formed on a side of the rear sheath 200 facing the back of the wearer's head such that the lugs are adjacent to two lateral outer sides of the sheath respectively. The lugs 220 and 230 are formed with a through-hole 221 and a through-hole 231 respectively. The two through-holes 211 and 231 are provided such that they are substantially coaxial with each other or their central axes include a small angle.

The cushion structure 700 is a single piece made of a plastic material. The cushion structure 700 comprises two loop portions 701 and 702. The loop portions are connected together by two connecting portions 703 and 704 such that the cushion structure 700 can be flexibly bent as required. Moreover, the loop portions are designed such that the cushion structure 700 can enable the wearer (especially his/her head) to feel more comfortable, and can also facilitate ventilation of the wearer's head and avoid sweating.

The cushion structure 700 has a supporting rib 720 adjacent to its left side and a supporting rib 730 adjacent to its right side. The supporting ribs 720 and 730 are formed on the loop portions 701 and 702 respectively. The supporting rib 720 has a pivotal pin 721, and the supporting rib 730 has a pivotal pin 731. The pivotal pin 721 has an exposing end and a root end connected to the supporting rib 720. The pivotal pin 731 has an exposing end and a root end connected to the supporting rib 730. The two exposing ends face each other. Each of the lugs 220 and 230 has an inner side facing the other's inner side. Each lug has an outer side opposite to its own inner side. By bending the cushion structure 700 from its lateral edges to its center, the pivotal pins 721 and 731 can be inserted into the through-holes 221 and 231 respectively.

The supporting ribs 720 and 730 are provided such that the distance between the root ends of the pivotal pins 721 and 731 is equal to or slightly less than the distance between the outer sides of the lugs 220 and 230. Therefore, after the root ends of the pivotal pins 721 and 731 are attached on the outer sides of the lugs 220 and 230 respectively and the pivotal pins 721 and 731 pass through the holes 221 and 231 respectively, the pivotal pin 721 in the hole 221 and the pivotal pin 731 in the hole 231 define a pivotal shaft about which the cushion structure 700 can be pivoted. Therefore, the cushion structure 700 is pivotally mounted on the rear sheath 200. It is appreciated by the person skilled in the art that more through-holed lugs and more pivotal pins can be provided in the sheath 200 and the cushion structure 700 respectively such that the latter can be more reliably pivoted. In an alternative embodiment, the lug and the pivotal pin can be interchanged with each other. For example, the lug can be provided in the cushion structure 700 and the pivotal pin can be provided in the sheath 200. In an alternative embodiment, the hole can be a blind hole provided on a side of the lug facing the root end of the pivotal pin.

Figure 10:
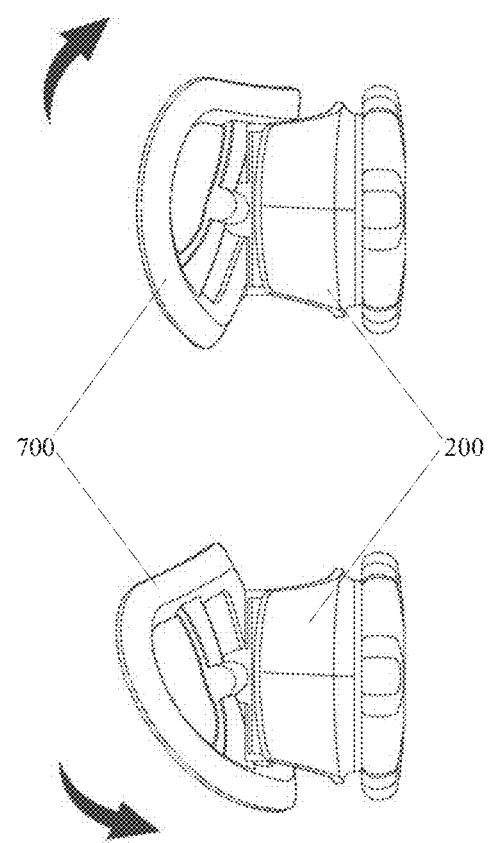
FIG. 10 schematically illustrates the cushion structure of FIG. 5 in two different pivoted states.

As shown in FIG. 10, because the cushion structure 700 can be pivoted upwards or downwards, the headband arrangement can be more fitted for the shape of the back of the wearer's head. The cushion structure 700 and the sheath 200 can be designed in their configuration such that the distance between the cushion structure 700 and the sheath 200 can be changed. In this way, an angle, by which the cushion structure 700 is pivoted relative to the sheath 200, can be adjusted. In a preferred embodiment, the cushion structure 700 can be pivoted relative to the sheath 200 in an angular range of about 90 degrees. For example, the cushion structure 700 can be pivoted upwards or downwards about 45 degrees relative to the horizontal plane. In an alternative embodiment, a sweat-absorbing pad can be provided on a side of the cushion structure 700 intending to contact the back of the wearer's head, to avoid slipping of the headband arrangement caused by sweat of the wearer. In one embodiment of the present application, the cushion structure 700 can be solely provided in a headband arrangement.

Although some specific embodiments of the present application have been described here, they are given for illustrative purpose only and should not be construed to limit the scope of the application in any way. Further, the described embodiments can be arbitrarily combined. Various alternations, changes and modifications can be thought out without departing from the spirit and scope of the present application.

The invention claimed is:

1. A headband arrangement for a welding helmet, comprising:
    a fixed attachment structure; and
    a helmet mounting structure cooperating with the attachment structure and comprising a lockable component, wherein:
        at least two stopping positions are defined longitudinally between the attachment structure and the helmet mounting structure,
        the helmet mounting structure is selectively switchable between an unlocking state and a locking state,
        in the unlocking state, the helmet mounting structure is slidable between the at least two stopping positions relative to the attachment structure, and
        in the locking state, the helmet mounting structure is locked to one of the at least two stopping positions relative to the attachment structure and is adapted to be held at one of the at least two stopping positions by a magnetic force generated between a pair of magnetic parts the pair of magnetic parts comprising a first magnetic part secured on the lockable component and a second magnetic part, the second magnetic part secured on the helmet mounting structure or the attachment structure.

2. The headband arrangement as recited in claim 1, wherein:
    the lockable component is mounted such that it is pivotable about a pivotal shaft in the helmet mounting structure;
    the helmet mounting structure is configured to be switched between the unlocking state and the locking state by rotating the lockable component; and
    in the locking state, the locking state is adapted to be maintained by a magnetic attractive or repulsive force generated between the first and second magnetic parts.

3. The headband arrangement as recited in claim 2, wherein:
    the first magnetic part comprises a first magnetic side;
    the second magnetic part comprises a second magnetic side;
    if the first magnetic side includes the same magnetic polarity as the second magnetic side, the first and second magnetic parts are arranged such that as the lockable component is pivoted from the locking state to the unlocking state the first magnetic side approaches the second magnetic side; or
    if the first magnetic side includes a magnetic polarity different than the second magnetic side, the first and second magnetic parts are arranged such that as the lockable component is pivoted from the locking state to the unlocking state the first magnetic side departs from the second magnetic side.

4. The headband arrangement as recited in claim 2, wherein:
    the lockable component comprises a tongue;
    the stopping positions are defined by several location holes formed in the attachment structure;
    the tongue enters one of the location holes when the helmet mounting structure is in the locking state; and
    the tongue leaves the location hole when the helmet mounting structure is in the unlocking state to allow the helmet mounting structure to be longitudinally slidable.

5. The headband arrangement as recited in claim 2, wherein:
    the helmet mounting structure comprises a bracket in which a socket is defined; and
    the pivotal shaft and the lockable component are disposed in the socket.

6. The headband arrangement as recited in claim 5, wherein the attachment structure comprises a location plate, location holes are provided in the location plate, and a rail is provided in the location plate to guide the helmet mounting structure.

7. The headband arrangement as recited in claim 1, wherein:

the lockable component is linearly movable in the helmet mounting structure, the helmet mounting structure is configured to be switched between the unlocking state and the locking state by linearly moving the lockable component, and in the locking state, the locking state is maintained by a magnetic repulsive force generated between the first and second magnetic parts.

8. The headband arrangement as recited in claim 7, wherein the lockable component is configured to be moved in a direction substantially perpendicular to a moving direction of the helmet mounting structure.

9. The headband arrangement as recited in claim 7, wherein the first and second magnetic parts are arranged such that they approach each other as the helmet mounting structure is being changed from the locking state to the unlocking state.

10. The headband arrangement as recited in claim 7, wherein:

the lockable component comprises a tongue, an elongated slot is formed in the attachment structure, the tongue protrudes into the slot, the stopping positions are defined by several notches formed at a side of the slot and in communication with the slot, in the locking state, the tongue enters one of the notches, and in the unlocking state, the tongue leaves the notch to allow the helmet mounting structure to be longitudinally slidable.

11. The headband arrangement as recited in claim 10, wherein in the unlocking state, the tongue is longitudinally movable in the slot.

12. The headband arrangement as recited in claim 10, wherein:

the helmet mounting structure comprises a bracket in which a socket is defined, and the lockable component and the second magnetic part are disposed in the socket.

13. The headband arrangement as recited in claim 1, wherein:

the lockable component is linearly movable in the helmet mounting structure, the pair of magnetic parts is disposed such that they are linearly movable in the helmet mounting structure, the pair of magnetic parts are configured to be moved in a direction substantially perpendicular to a moving direction of the lockable component and parallel to a moving direction of the helmet mounting structure, the movement of the pair of magnetic parts is in association with the movement of the lockable component such that the helmet mounting structure can be switched between the unlocking state and the locking state, and in the locking state, the helmet mounting structure is kept to be locked by a magnetic repulsive force generated between the pair of magnetic parts.

14. The headband arrangement as recited in claim 13, wherein:

the lockable component comprises a tongue, the stopping positions are defined by several location holes formed in the attachment structure, the tongue enters one of the location holes in the locking state, and the tongue leaves the location hole, in the unlocking state, to allow the helmet mounting structure to be longitudinally slidable.

15. The headband arrangement as recited in claim 13, wherein:

the lockable component in the helmet mounting structure comprises a first key part and a second key part, the pair of magnetic parts comprise the first magnetic part embedded in the first key part and the second magnetic part embedded in the second key part, and the first and second magnetic parts approach each other as the helmet mounting structure is being changed from the locking state to the unlocking state.

16. The headband arrangement as recited in claim 15, wherein at least one of the first and second key parts is provided with a rod portion by which the lockable component can be driven to move.

17. The headband arrangement as recited in claim 16, wherein:

the rod portion comprises a linear section and an arc-shaped section, and the rod portion is inserted through a through-hole formed in the lockable component such that the rod portion is configured to be moved substantially perpendicularly to the moving direction of the lockable component so as to pass through the through-hole.

* * * * *